United States Patent
Sonntag et al.

(10) Patent No.: US 8,758,415 B2
(45) Date of Patent: Jun. 24, 2014

(54) ANGULARLY STABLE FIXATION OF AN IMPLANT

(75) Inventors: Robert Sonntag, Helmstadt-Bargen (DE); Klaus Dorawa, Schonkirchen (DE); Nils Zander, Eckernförde (DE); Jörg Mayer, Niederlenz (CH); Urs Weber, Olten (CH); Andrea Müller, Winterthur (CH)

(73) Assignee: Stryker Trauma GmbH (DE)

( * ) Notice: Subject to any disclaimer, the term of this patent is extended or adjusted under 35 U.S.C. 154(b) by 864 days.

(21) Appl. No.: 12/678,374

(22) PCT Filed: Sep. 18, 2007

(86) PCT No.: PCT/EP2007/008130
§ 371 (c)(1),
(2), (4) Date: Mar. 16, 2010

(87) PCT Pub. No.: WO2009/036783
PCT Pub. Date: Mar. 26, 2009

(65) Prior Publication Data
US 2010/0211111 A1    Aug. 19, 2010

(51) Int. Cl.
*A61B 17/80* (2006.01)
(52) U.S. Cl.
USPC .......................................... 606/286
(58) Field of Classification Search
USPC ............. 606/87, 96–98, 104, 281, 289, 291;
264/442–445; 156/73.1–73.6; 228/1.1,
228/110.1
See application file for complete search history.

(56) References Cited

U.S. PATENT DOCUMENTS

| | | | |
|---|---|---|---|
| 3,038,358 A * | 6/1962 | Jones | 228/1.1 |
| 4,248,232 A * | 2/1981 | Engelbrecht et al. | 606/169 |
| 4,590,928 A * | 5/1986 | Hunt et al. | 606/916 |
| 4,781,183 A | 11/1988 | Casey et al. | |
| 4,905,680 A | 3/1990 | Tunc | |
| 5,163,960 A | 11/1992 | Bonutti | |
| 5,593,425 A | 1/1997 | Bonutti et al. | |
| 5,688,285 A * | 11/1997 | Yamada | 606/104 |
| 6,010,525 A | 1/2000 | Bonutti et al. | |
| 6,059,817 A | 5/2000 | Bonutti et al. | |
| 6,206,883 B1 | 3/2001 | Tunc | |
| 6,464,713 B2 | 10/2002 | Bonutti | |
| 6,503,267 B2 | 1/2003 | Bonutti et al. | |
| 6,519,500 B1 * | 2/2003 | White | 700/119 |

(Continued)

FOREIGN PATENT DOCUMENTS

JP    9149906 A    6/1997
WO    98/42988 A1    10/1998

(Continued)

*Primary Examiner* — Anu Ramana
(74) *Attorney, Agent, or Firm* — Lerner, David, Littenberg, Krumholz & Mentlik, LLP

(57) ABSTRACT

A system and method of angularly stable fixation of an implant on a bone includes the steps of making at least one hole in the bone by means of a bone drill. An implant is placed on the bone in a desired position and joining the implant with the bone, such that the implant is prevented from rotation about its attachment point. A system is provided for use in the above described method. The system comprises a bone drill, an implant and a sonotrode for angularly stable fixation of the implant on the bone. The system can further comprise a joining element to join the implant with the bone.

14 Claims, 10 Drawing Sheets

(56) References Cited

U.S. PATENT DOCUMENTS

| | | |
|---|---|---|
| 6,605,090 B1 | 8/2003 | Trieu et al. |
| 6,623,487 B1 | 9/2003 | Goshert |
| 6,691,909 B2 * | 2/2004 | Skogsmo et al. .......... 228/111.5 |
| 6,692,498 B1 | 2/2004 | Niiranen et al. |
| 7,172,595 B1 | 2/2007 | Goble |
| 7,229,445 B2 | 6/2007 | Hayeck et al. |
| 7,335,205 B2 | 2/2008 | Aeschlimann et al. |
| 7,491,236 B2 * | 2/2009 | Cragg et al. .............. 623/17.11 |
| 7,717,945 B2 * | 5/2010 | Jensen et al. ................. 606/284 |
| 2004/0030341 A1 | 2/2004 | Aeschlimann et al. |
| 2004/0053196 A1 | 3/2004 | Mayer et al. |
| 2004/0167521 A1 | 8/2004 | De Windt |
| 2006/0030852 A1 | 2/2006 | Sevrain |
| 2006/0167495 A1 | 7/2006 | Bonutti et al. |
| 2006/0217765 A1 | 9/2006 | Bonutti et al. |
| 2006/0235470 A1 | 10/2006 | Bonutti et al. |
| 2007/0260250 A1 | 11/2007 | Wisnewski et al. |
| 2007/0270833 A1 | 11/2007 | Bonutti et al. |
| 2008/0021474 A1 | 1/2008 | Bonutti et al. |
| 2008/0039845 A1 | 2/2008 | Bonutti et al. |
| 2009/0024161 A1 | 1/2009 | Bonutti et al. |

FOREIGN PATENT DOCUMENTS

| | | |
|---|---|---|
| WO | 02/069817 A1 | 9/2002 |
| WO | 2004/017857 | 3/2004 |
| WO | 2005/079696 A1 | 9/2005 |
| WO | 2007/092869 A2 | 8/2007 |

* cited by examiner

ANGULARLY STABLE FIXATION OF AN IMPLANT

CROSS REFERENCE TO RELATED APPLICATION

The present application is a national phase entry under 35 U.S.C. §371 of International Application No. PCT/EP2007/008130, filed Sep. 18, 2007, published in English. The disclosure of said application is incorporated by reference herein.

BACKGROUND OF THE INVENTION

1. Field of the Invention

The invention relates to a system and method of fixation of an implant to a bone. The invention particularly relates to a system and method of angularly stable fixation of an implant to a bone.

2. Brief Description of the Prior Art

It is generally known that fractures are treated by fixation of the broken bones. The individual fragments of the bone are lined up to each other so that the separated parts can grow together again. It is necessary that the parts remain relatively stable with respect to each other over a time period to allow the healing. It is possible in many cases to fix the fragments of the fractured bone via a rigid cast such as a plaster cast on the outside of the broken part of the body. The broken bone pieces are aligned with each other and held in position by the rigid cast. In some cases, particularly for more complicated fractures, it is necessary to connect the individual broken bone pieces directly with each other. In these cases, the fracture is fixed or reduced via an invasive procedure wherein an implant is installed within the body with screws or nails.

It has turned out, however, that fixed bone parts do not always grow together as desired. In addition, the conventional invasive methods of fracture fixation are accompanied by relatively high trauma and loss of blood. Furthermore, there is a need for a device for fixation of periprothetic fractures in immediate proximity of implants, particularly joint implants.

Fixing plates have been suggested for use in the methods mentioned above. Plates are first pre-formed according to the individual fracture situation outside the patient and then connected via an operation to the fractured bone or the bone fragments by nails or screws. These plates have the additional advantage that they can fix particularly smaller fragments and stabilize the fracture. This way, in case of more complicated fractures, the fractured pieces can be reliably connected with each other or with several fragments.

However, these fixing plates cannot be fastened ideally. Particularly when the fracture involves the musculoskeletal system and the fractured pieces are exposed to different shearing forces in the course of the movement. Thus, there is a need for implants with improved fixation for fractures involving musculoskeletal system.

SUMMARY OF THE INVENTION

The present invention provides a system comprising an implant plate from a polymeric material, a bone drill and a sonotrode. The system further comprises a pin from a polymeric material, which is provided to join the implant plate with the bone. The pin can be selected from the group consisting of a pin, a conically formed pin, a plug, a springing up hook plug, a multi-toothed plug, a screw, a conically formed screw, a graded pin, a twice formed pin, a triangular formed or asymmetrically formed pin, or a pin having a thickened head.

In case the polymeric pin shall be melted together with the implant, the implant material should be the same or at least similar to the material of the polymeric pin.

According to an exemplary embodiment the present invention provides a system that includes a plate having an opening formed therein. The opening is rotationally non-symmetric. The system also includes a drill. The drill is adopted to form the opening and a hole in a bone adjacent the plate. The system further includes a pin insertable in the opening. A sonotrode is also included in the system. The sonotrode is adapted to apply energy to the pin so as to melt at least a portion of the pin thereby attaching the pin in the bone and to the plate such that rotational movement of the plate is prevented.

Yet another embodiment of the invention provides an angularly stable implant for fracture fixation. The implant includes a plate adapted to mount on a bone. The plate and the bone have a first opening and a second opening respectively. The first opening and the second opening are substantially aligned and have a rotationally non-symmetric shape. A pin shaped to be inserted in the first opening and second opening and capable of receiving energy to melt at least a portion of the pin is provided. The melted material of the pin is capable of solidifying in the first opening and the second opening to weld the pin to the bone and the plate to form an angularly stable implant that does not rotate with respect to the bone.

The invention also includes a method generally having the following steps: Making at least one hole in the bone, connecting an implant with the bone angle stably at a desired position at the bone and finally placing the implant. In accordance with an exemplary embodiment a jig can be used at the method to establish at least one hole in the bone or also lead means with the help of which the implant is fastened to the bone angle stably. In accordance with a further exemplary embodiment a marking can be set, which at first serves to line up the jig or the matrix on the bone for preparing the at least one hole in the bone, and then to align with the marking and place thus exactly the implant. In accordance with another exemplary embodiment of the method according to the invention the implant material is liquefied by applying ultrasound energy to the material so that the implant material flows into the at least one hole and fixes the angular stability of the implant placed at the bone. By the ultrasound energy also a joining element can be liquefied, which is placed through the implant and into the at least hole formed in the bone, so that it is, on the one hand, reliably established in the bone and, on the other hand, melted together with the implant material at its back end.

According to another embodiment the present invention also includes a method of fracture fixation wherein the implant is placed on the bone, the implant having a first vertical axis normal to a top surface of the implant. A first and a second hole are drilled in the bone, the first hole and the second hole forming a first angle and a second angle respectively with the vertical axis. At least a portion of the implant is melted and pushed in the first hole and the second hole. The melted implant material is allowed to solidify in the first hole and the second hole to obtain an angularly stable attachment of the implant to the bone.

Another method of fracture fixation teaches placing a plate on a bone and forming at least one opening in the plate and the bone. The opening is rotationally non-symmetric. A pin is inserted in the opening and energy is applied to the pin to melt at least a portion of the pin thereby attaching the pin in the bone and to the plate such that rotational movement of the plate is prevented.

Another method of fracture fixation teaches placing a plate on a bone the plate having a vertical axis extending through the thickness of the plate. Forming in the bone a first opening at a first angle with the axis and a second opening at a second angle with the vertical axis. Melting the plate by application of energy and flowing the melted material of the plate in the first opening and the second opening to form an angularly stable connection between the plate and the bone upon solidification.

It is an object of the invention to provide a system and a method of fixation of an implant plate to a bone, in which the implant plate is connected with the bone in an angularly stable manner.

This object is achieved by the subject matter of each independent claim. Further exemplary embodiments are described in the respective dependent claims.

BRIEF DESCRIPTION OF THE DRAWINGS

The invention is explained by means of exemplary embodiment and with reference to the following drawings.

DETAILED DESCRIPTION

Figure 1:
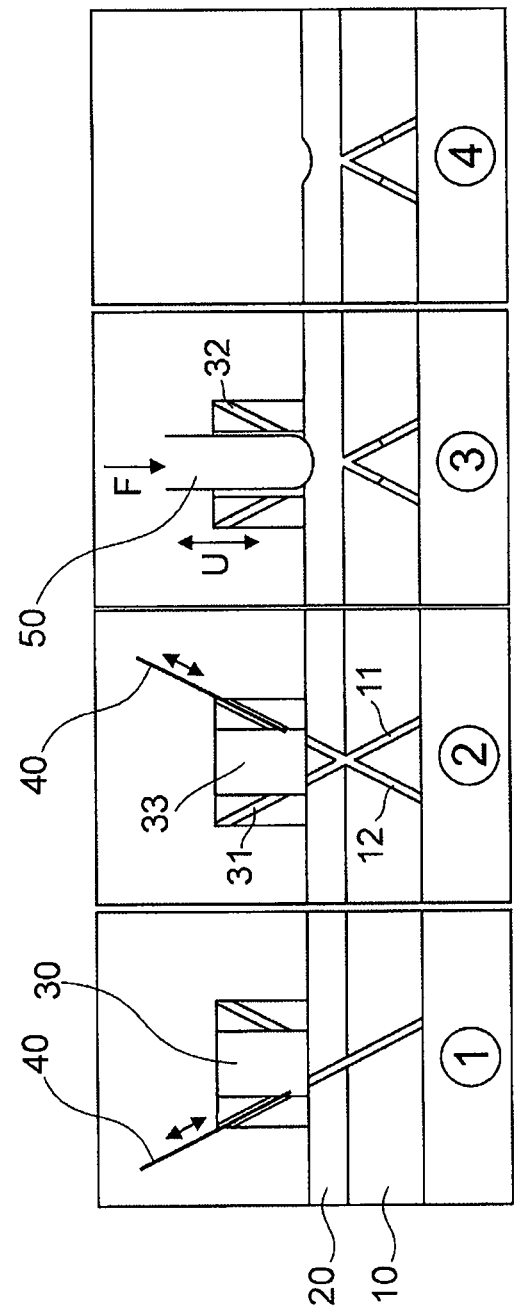
FIG. 1 shows schematically, in four frames, a method of angularly stable fixation of an implant on a bone in accordance with a first exemplary embodiment of the invention.

FIG. 1 shows an implant plate 20 mounted directly on cortical bone 10. The implant plate 20 may be made from materials such as medical grade plastic, for example, from a polylactid material (PLLA, PLDLA). The used material might be resorbable. Each one of the FIGS. 1-10 has four frames showing the steps of the method illustrated in each of the figures. The implant plate 20 and the bone 10 are drilled through with the help of a Kirschner wire 40 such that the drilled openings 11 and 12 cross each other. The drilled openings 11 and 12 should preferably cross at the interface of the implant plate 20 and the bone 10. A drill jig 30 or other suitable guiding device can be used to guarantee that the crossing point is at the interface of the plate 20 and the bone 10. As represented in frame 1 in FIG. 1, the implant plate 20 is placed on the bone 10. The jig 30 is placed on the plate 20. The jig 30 has two channels 31 and 32 through which a Kirschner wire or alternatively a drill can be advanced to drill openings 11 and 12. Furthermore, the jig 30 has a through hole 33, which accepts and guides a sonotrode.

First the Kirschner wire 40 is reciprocated back and forth through the channel 31 of the jig 30 to form a first opening 11 both through the implant plate 20 and through the bone 10.

Next, the Kirschner wire 40 is reciprocated back and forth, as seen in frame 2 in FIG. 1, through the second channel 32 of the jig 30 so that a second opening 12 is formed in the implant plate 20 and the bone 10. The two openings 11, 12 cross at the interface plane between the implant plate 20 and the bone 10.

As shown in frame 3 in FIG. 1 the jig 30 is located on the implant plate 20. Next, by means of a sonotrode 50 led in the through hole 33, a pressure force F and a vibration U is applied, so that the implant material of the implant plate 20 liquefies in the area of the drilled openings 11, 12 and a part of the material flows into these openings. By virtue of the material flowing in the openings 11 and 12, the plate 20 is fixed to the bone 10 as shown in frame 4. The plate 20, fixed to the bone 10, in the above described manner is angularly stable, i.e., the plate cannot rotate. The inclination of the channels 31, 32 in the jig 30 are dependent on the thickness of the implant plate 20. The bone plate 20 is received in the bone 10 like the root of a tooth in the jaw. A variation of this exemplary embodiment of the method may have four drillings/openings placed at 90 degrees from each other instead of the two opposite drillings. The thickness of plate 20 may be thicker or thinner as required. This way more polymer can flow into the openings 11 and 12 in the bone 10. The aim is to have sufficient plate thickness left after the impact of the pressure force F and the ultrasound vibrations U has produced ample melting of the plate 20. Through this shear stress can be avoided at later load.

Figure 2:
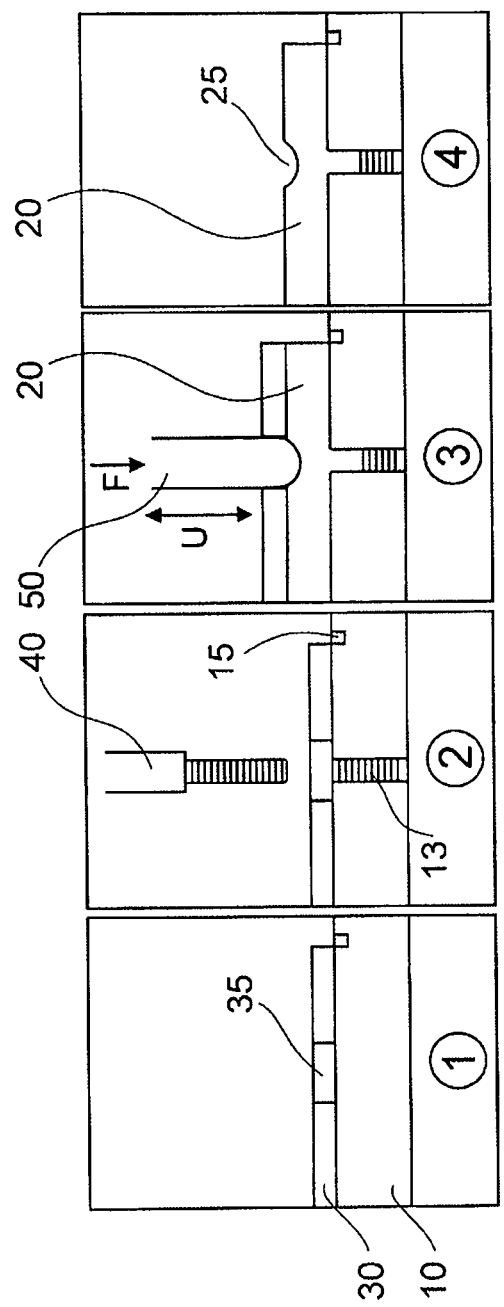
FIG. 2 shows schematically a second exemplary embodiment of a method in accordance with the invention.

FIG. 2 shows a second exemplary embodiment of the invention. Here the implant plate 20 is connected with the bone 10 in an angularly stable manner. Frame 1 shows a drill jig 30a placed on the bone 10. Next, a marking 15 is placed on the bone 10. Then a tapped hole 13 is cut into the bone 10 by means of a screw drill or tap 40 as shown in frame 2 in FIG. 2. The screw drill 40 is inserted in and guided by opening 35 in the jig 30a to form the tapped hole 13 in the bone 10. The marking 15 is then used to place the implant 20 together with the jig 30a in the desired location. Next the sonotrode 50 is aligned with the opening 35 in the jig 30a which was already used for making hole 13 using the screw tap 40. Frame 3 in FIG. 2 shows use of the sonotrode 50 to melt (i.e., liquefy) the material of the implant plate 20 and flow the melted material into the threaded hole 13 in the bone 10. The melting is done by applying pressure F and the vibrations U to the implant 20 via the sonotrode 50. Frame 4 of FIG. 2 shows the implant 20 attached to bone 10 using the method illustrated in FIG. 2.

Unlike the first exemplary embodiment no opening/hole is cut into the implant plate 20 itself and consequently formation of polymer debris is prevented. Here only the bone 10 is provided with a threaded hole 13. The drilling point and the point to which the sonotrode 50 is attached is defined by a jig 30a which is aligned with the marking 15. The process described above may be repeated to form more than one holes, in which the implant material then flows into and stiffens. The sonotrode 50 produces the energy by means of ultrasound vibrations U and a force F which is suitable to liquefy the implant material in the area of the threaded opening 13. The location of the threaded hole 13 is visible as a slight depression 25 in the implant plate 20 where the sonotrode 50 was in contact with the implant plate 20. This depression 25 can be avoided or at least the expression reduced by strengthening the material of the plate 20 at the respective impact point of the sonotrode.

Figure 3:
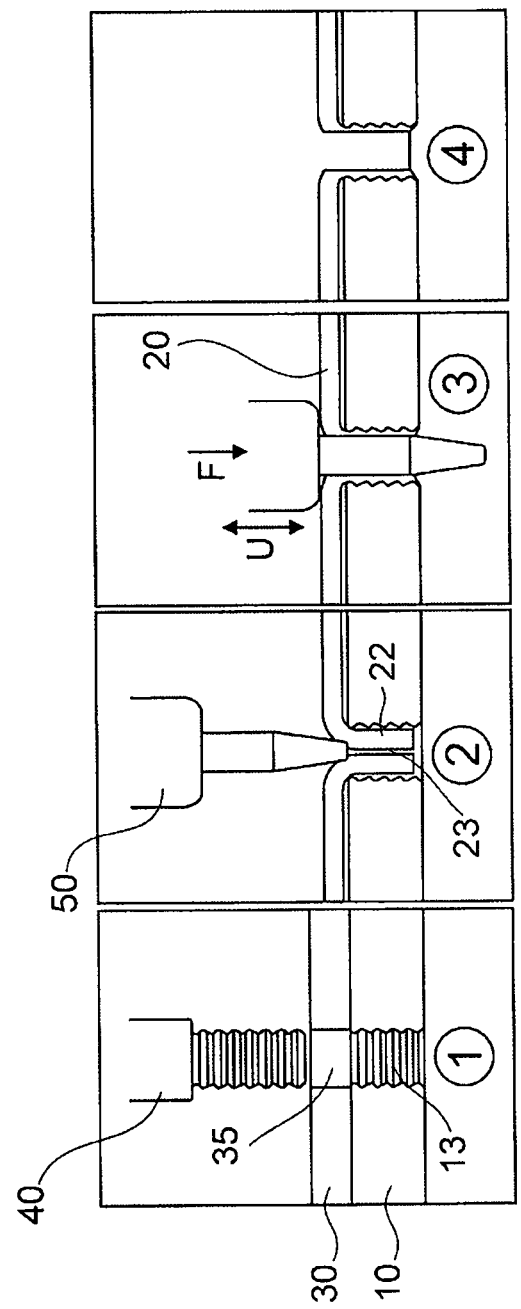
FIG. 3 shows schematically a third exemplary embodiment of a method in accordance with the invention.

FIG. 3 shows a third exemplary embodiment that illustrates the method according to the invention. The third embodiment uses pre-formed implant plate 20. The plate 20 has the geometry that also fulfils the functions of the polymeric pins of other exemplary embodiments. The implant plate 20 of the third exemplary embodiment comprises protrusions 22 that are sized to be slid into holes 13 in the bone 10. The location of the protrusions 22 in the implant plate 20 requires a very exact and corresponding positioning of thread holes 13 in the bone 10. This can be managed, for example, by means of a jig 30b.

As shown in frame 1 in FIG. 3, first the jig 30 is placed on the bone 10. Next, threaded openings 13 are formed in the bone 10 using screw tap 40. The holes 35 in the jig 30b are used to guide screw tap 40 during formation of openings 13. Next, the implant plate 20 is placed on bone 10 such that protrusions 22 project into each drilled hole (i.e., opening) 13. The implant material is now liquefied by means of a sonotrode 50 which is formed with a pointed front end that is inserted in the protrusions 22. This results in the implant material being melted and conforming to the threads formed in the opening 13 in the bone 10, as shown in the frames 2 and 3 in FIG. 3. In this third exemplary embodiment a preliminary stabilization of the fracture is achieved by inserting the protrusions 22 of the implant plate 20 into the openings 13 in the bone 10. The protrusions 22 may be formed in shape of a cone with a central through hole 23, i.e., a through hole 23 may be formed through the implant plate 20 and lengthwise through the protrusions 22. The tip of the sonotrode 50 fits into this hole 23. The tip is greater in diameter than the opening in the plate 20 and does exert a pressure on the implant material not only in axial but also in radial direction within the threaded openings 13 in the bone 10 so that the material flows reliably into the threads of the screw thread in the bone 10. The implant 20 of the third embodiment represents a very stable system because it only consists of a single component.

Figure 4:
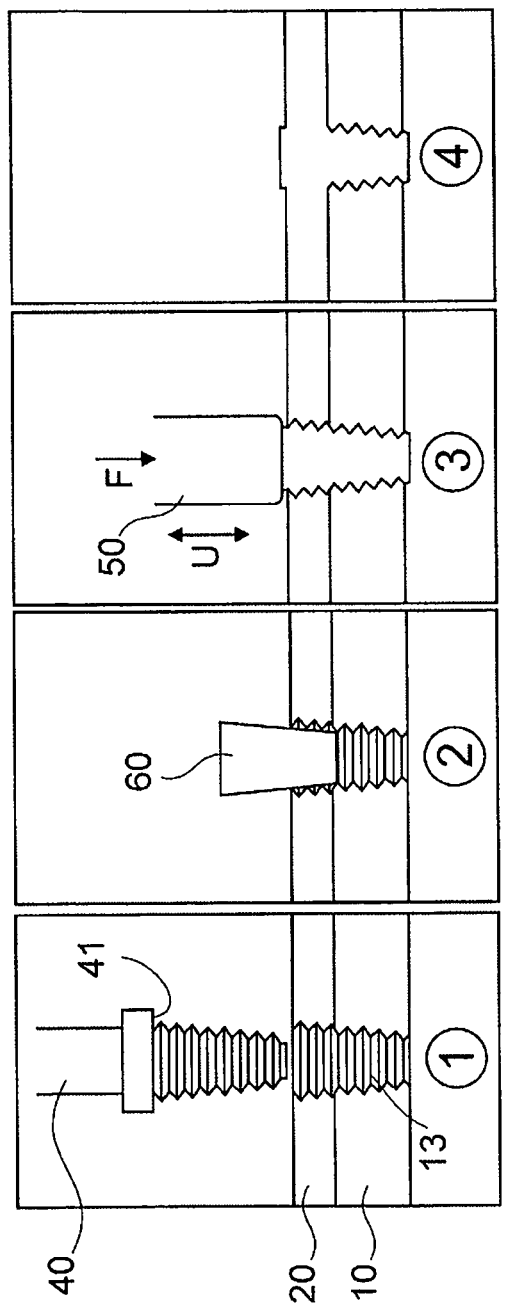
FIG. 4 shows schematically a fourth exemplary embodiment of a method in accordance with the invention.

Exemplary embodiments described hereafter use an additional joining element 60. The joining element 60 is used to connect the implant plate 20 with the bone 10. The fourth exemplary embodiment of the present invention is schematically represented in four frames of FIG. 4. A conical screw tap 40 which makes a conical threaded hole 13 in the implant plate 20 and through the bone 10 simultaneously is shown in frame 1 in FIG. 4. Next, in frame 2, a conical pin 60 is shown inserted into the hole 13. The cone angle of the conical pin 60 matches the angle of the screw tap 40. Frame 3 in FIG. 4 shows the pin 60 being liquefied by means of the sonotrode 50. The liquefied material of the pin 60 fills out the cavities in the threaded opening 13 and also melts together with the implant material of the implant plate 20. The penetration depth of the screw tap 40 depends on the plate thickness and is correspondingly defined by a stop 41. The threaded opening 13 offers a simple possibility for the structuring of the bone 10 and at the same time supports the melt process by creation of defined places with high local energy density.

Figure 5:
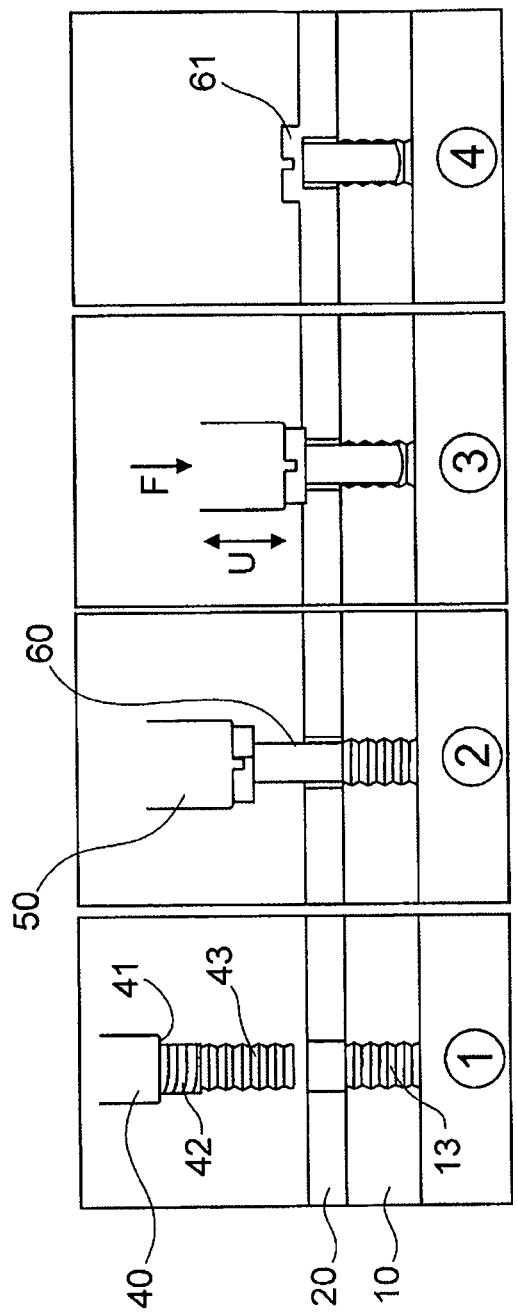
FIG. 5 shows schematically a fifth exemplary embodiment of a method in accordance with the invention.

FIG. 5 shows successive frames of the fifth exemplary embodiment of the invention. Similar to the fourth exemplary embodiment, here a hole (alternatively referred to as an opening) 13 is drilled by means of a screw tap 40 through the implant plate 20 and the bone 10 simultaneously. A screw 60 is screwed into this hole 13. This way the implant plate 20 is preliminarily stabilized in the bone 10. A final angularly stable attachment of the implant to the bone 10 is achieved by applying a force F and an ultrasound vibration U by means of a sonotrode 50 to the screw 60. Thereby, the screw thread of the screw 60 is liquefied and the liquefied material moulds to conforms to the threads in the hole 13 in the bone 10. Further the screw head 61 is melted together with the adjacent surface of the implant plate 20.

Since the material of the inserted screw 60 liquefies due to the application of the ultrasound vibration U and the force F, the shaft of the inserted screw may be made smooth in a variation of this embodiment, i.e. the threads of the threaded pin are optional. In addition, the processing of the implant plate 20 and the bone 10 can be done by a drill-tap-combination. The drilling depth is provided by means of a drilling stop 41. The front tap part 43 produces the threaded hole 13 in the bone 10 and the following drill part 42 of the drill-tap-combination produces a smooth hole in the implant plate 20. The material of the polymeric pin 60 melted and then stiffened in the threaded hole 13, offers a good anchorage of the implant plate 20 in the bone 10. By welding together the pin head 61 or the screw head 61 with the implant plate 20 an angularly stable fixation of the implant in the bone 10 is ensured.

Figure 6:
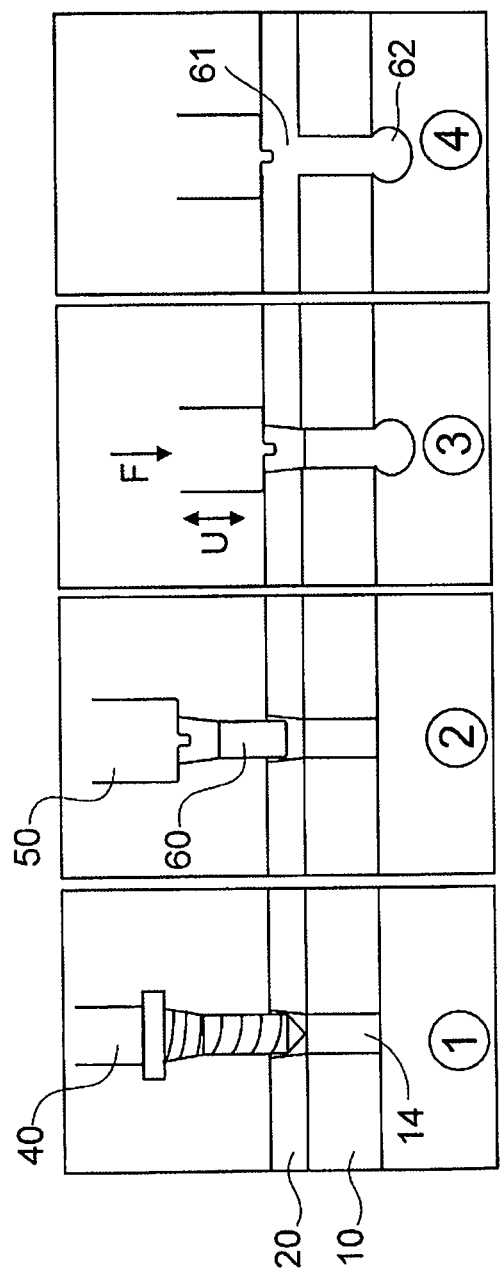
FIG. 6 shows schematically a sixth exemplary embodiment of a method in accordance with the invention.

The sixth exemplary embodiment of the invention is shown in FIG. 6. This method practiced using the sixth embodiment is similar to the method in accordance with the fifth exemplary embodiment. The difference here is that in place of the threaded hole 13, a through hole 14 is formed in the bone 10. The through hole 14 is drilled through the implant plate 20 and cortical portion of the bone 10. The simple procedure for preparing of the bone 10 and the implant plate 20 represents a principal benefit of this solution. This simple procedure of making a smooth hole 14 is performed using a drill 40 as shown in frame 1 in FIG. 6. Next the surgeon inserts a polymeric pin 60 in the hole 14 and pushes it by means of a sonotrode 50. The diameter of the polymeric pin 60 is slightly greater than that of the hole 14 in the bone 10. The diameter difference ideally is about 0.1 to 0.2 mm.

The application of the ultrasound energy via the sonotrode 50 melts the material of the pin 60 where the pin 60 comes in contact with the bone 10. The melted material is transported by the movement of the pin 60 through the hole 14 and below the cortical portion of bone 10. The melted material stiffens there again and provides a thickening 62 below the cortical portion of bone 10 (for example cancellous bone) as a result of which a reliable anchorage is achieved. The polymeric pin 60 is also welded with the polymeric material of the implant plate 20 by virtue of the fact that the opening in the implant plate 20 and the head 61 of the polymeric pin 60 are conical and form a close fit and are welded together under the action of the ultrasonic energy.

Figure 7:
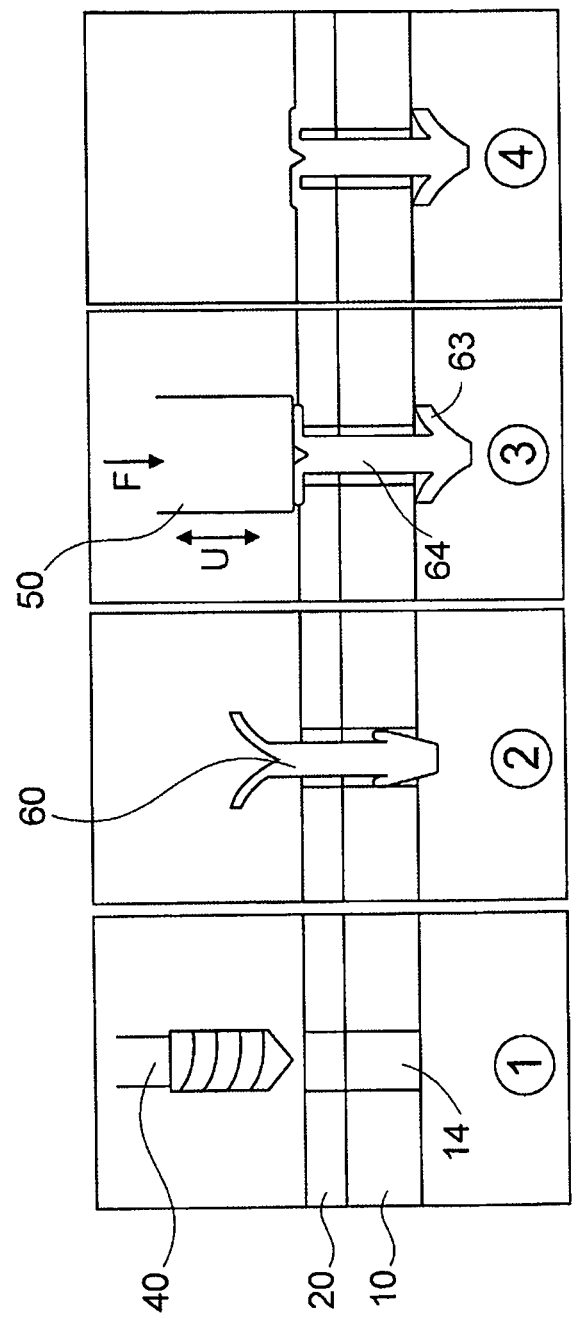
FIG. 7 shows schematically a seventh exemplary embodiment of a method in accordance with the invention.

The seventh exemplary embodiment of the invention is shown in FIG. 7. In the seventh embodiment, a plug 60 is used instead of a polymeric pin or a screw of the previous embodiments. As shown in frame 1 in FIG. 7, a hole 14 is formed into the implant plate 20 and the bone 10 simultaneously. A drill 40 is used to form the hole 14. A plug 60 is inserted in hole 14 as shown in frame 2 in FIG. 7. At first, latches 63 which are formed at the leading end of the plug 60 are pressed against the shaft 64 of the plug. As soon as the leading edge has penetrated through the cortical portion of the bone 10 into the cancellous bone, the latches 63 expand away from the shaft 64 and anchor the plug 60 in the bone 10.

As illustrated in frame 3 in FIG. 7, the back end of the plug 60 can then be liquefied by subjecting it to the ultrasonic energy via the sonotrode 50 and thereby welding it to the implant material. The result is a snap-in connection of the plate 20 with the cortical part of bone 10. To prevent the polymeric plug 60 from being pushed during the process of welding and consequently becoming loose in the bone 10, a cord (not shown) can be provided which is integrated into the plug. Using the cord, the plug 60 can be drawn towards the sonotrode 50 during the melting process. This way the plug 60 can be used so that the elastic latches are held under tension against the cortical portion of bone 10 at the leading edge of the plug 60.

Figure 8:
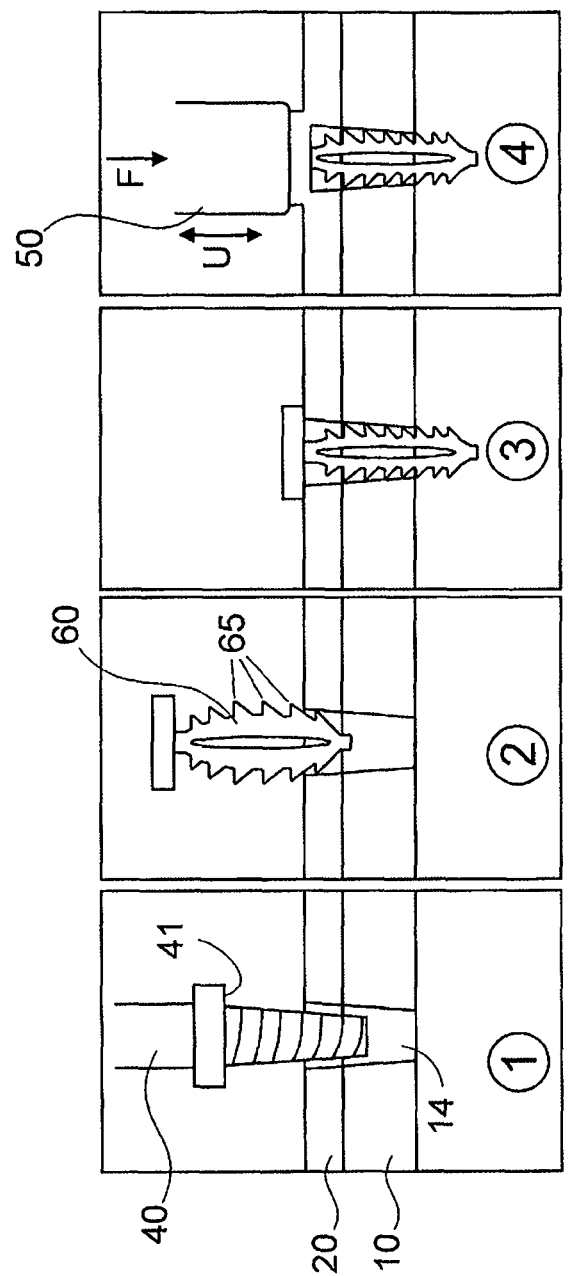
FIG. 8 shows schematically an eighth exemplary embodiment of a method in accordance with the invention.

FIG. 8 shows the eighth exemplary embodiment of the invention. In the eighth exemplary embodiment a plug 60 is used for the anchorage of the implant plate 20 on the bone 10. In this case the plug 60 includes teeth 65 on the surface of the shaft portion of the plug 60. The shaft of the plug 60 has a longitudinal slit that allows the shaft to be pressed in radial direction. This allows the plug 60 to be pushed through a hole 14, which is smaller in diameter than the shaft diameter of the plug 60 in its non-compressed state.

Ideally, a hole is drilled both into the implant plate 20 and into the bone 10 by means of a conical bone drill 40. A stop 41 at the drill 40 limits the depth of the hole 14 and prevents it from being formed too deeply in the bone 10. The implant plate 20 is anchored in the bone 10 by inserting the plug 60 deeply into the hole 14. The teeth 65 located adjacent to the head of the plug 60 act as hooks which abut the inside of the bone 10. On the other hand, the teeth which are formed along the shaft lodge into the bone within the drilling 14. The plug 60 is welded, by means of a sonotrode 50, with the implant plate 20. The conical shape of the hole allows anchoring of the plug in the hole 14. A suitably fine geometry of the teeth 65 or lamellae for the anchorage of the plug 60 can reduce a play which may arise when the sonotrode 50 is pushed on the plug 60 to weld it together with the implant plate 20.

Figure 9:
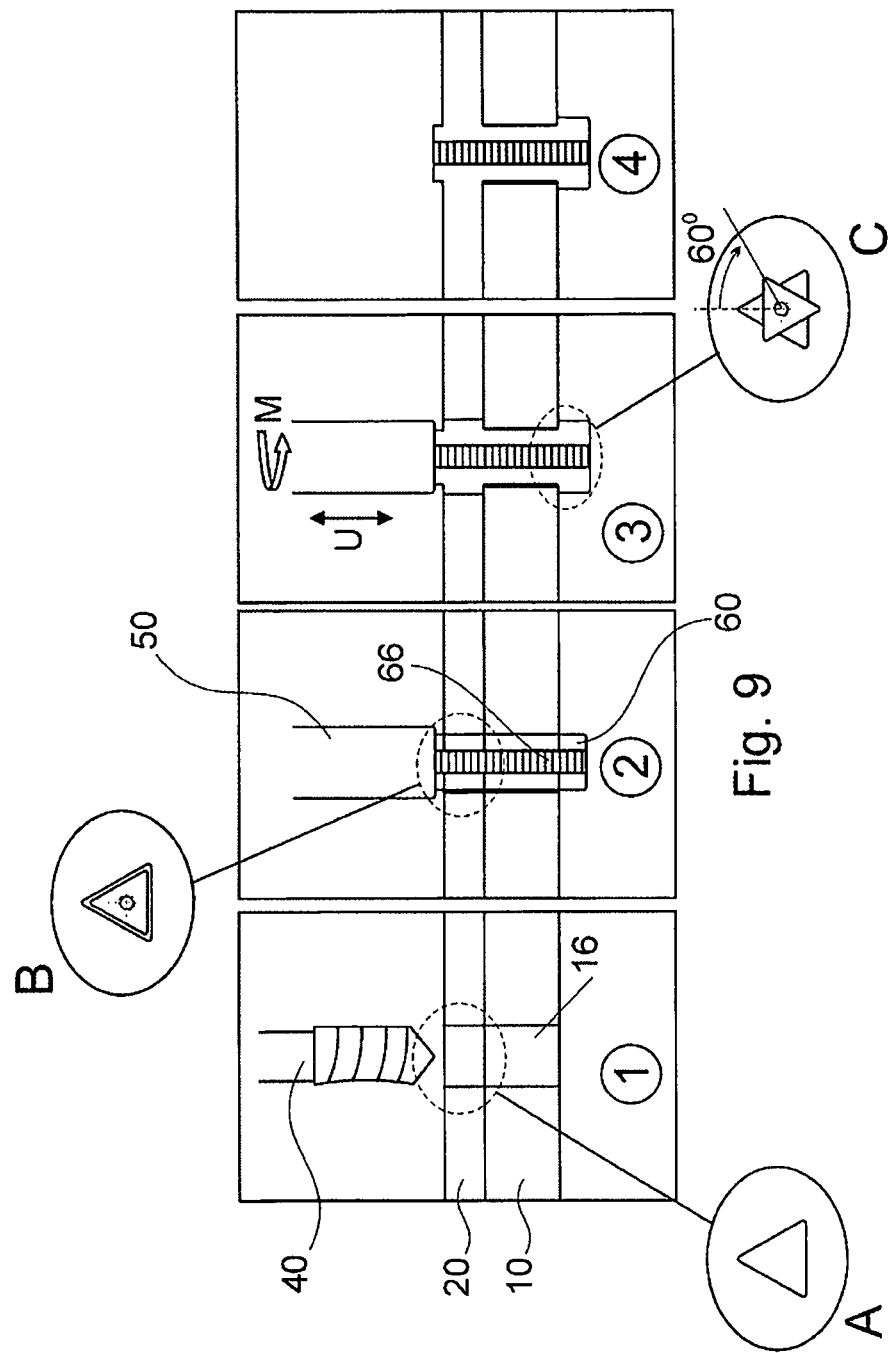
FIG. 9 shows schematically a ninth exemplary embodiment of a method in accordance with the invention.

FIG. 9 shows schematically the ninth exemplary embodiment of the invention. One feature of this embodiment is the triangular hole 16 formed in the bone 10. A hole without rotational symmetry and larger than the triangular hole 16 is formed in the implant plate 20. Alternatively, non-rotational-symmetric holes of any other shape may be formed in the implant plate 20 and the bone 10. Non-rotational-symmetric holes (or alternatively rotationally non-symmetric holes) are holes in which a pin of complimentary shape can not be rotated by virtue of the shape and matching size of the pin and the hole. An example of the rotationally non-symmetric hole would be non-circular i.e. an oblong hole or a triangular hole. The matching pins would be oblong or triangular respectively and would be sized to be a close fit in the hole. The holes may be formed, for example, by means of a drill 40 which is ground on one side or is swinging eccentrically, as shown in frame 1 in FIG. 9. Other known methods available to one skilled in the art may be used to make the holes. A polymeric pin 60 is then introduced in the hole 16 with a cross section similar to that of the hole 16. The polymeric pin 60 has a threaded hole 66 extending in longitudinal direction in the centre portion of the pin 60. An appropriately formed tip of the sonotrode 50 is connected to the threaded hole 66. The polymeric pin 60 is completely screwed on the tip of the sonotrode such that it cannot be screwed any further.

Furthermore the length of the pin 60 is such that the pin 60 projects into the bone 10 beyond the cortical bone layer. In this position a torque M is applied together with the ultrasound vibration U from the sonotrode 50 and the assembly of sonotrode and polymeric-pin is rotated by about 60 degrees. Here, a tool combination of a sonotrode and a drill is conceivable.

Finally, the pin 60 would melt in the area that is in the cortical bone layer of the bone 10. However, the polymeric pin would encounter much less resistance to rotation in the areas of the pin 60 that extend beyond the cortical layer of bone 10 at both ends. Since the leading edge of the pin 60 is in the softer portion of the bone located next to the cortical bone layer, the rotation of the assembly of sonotrode 50 and the pin 60 results in dislocation of the pin portion that is located in softer bone and seen in frame 3 of FIG. 9. Similarly, the portion of the pin 60 that is located in the implant plate 20 is also dislocated in relation to the portion of the pin 60 that is adjacent the cortical portion of the bone 10. This way the polymeric pin 60 is locked from below the cortical bone layer and on top in the implant plate 20. Therefore, the pin 60 is prevented from being pulled out of the bone 10. Additional locking of the polymeric pin 60 is achieved by melting the pin 60 together with the material of the implant plate 20. As a result an angularly stable connection of the implant plate 20 to the bone 10 is achieved.

Frame 1 of FIG. 9 illustrates the method step in which a hole 16 is formed in the implant plate 20 and the bone 10. The detail A shows the cross-section of the hole 16. The polymeric pin 60 which is screwed on to the tip of the sonotrode all the way up to the stop and put into the hole 16, is shown in frame 2 of FIG. 9. Detail B shows a cross-sectional view of the hole 16 with the polymeric pin 60 inserted therein. Frame 3 of FIG. 9 shows the condition of the polymeric pin 60 after a torque M was applied by the sonotrode 50. Distortion of the end regions of body of the pin 60 relative to the central region is visible in the area of the implant plate 20 and below the cortical portion of the bone 10. Detail C shows a bottom view of the leading end of the polymeric pin 60 which is twisted by 60 degrees relatively to the hole 16. Frame 4 of FIG. 9 finally shows the polymeric pin in its final position welded together with the implant plate 20.

Figure 10:
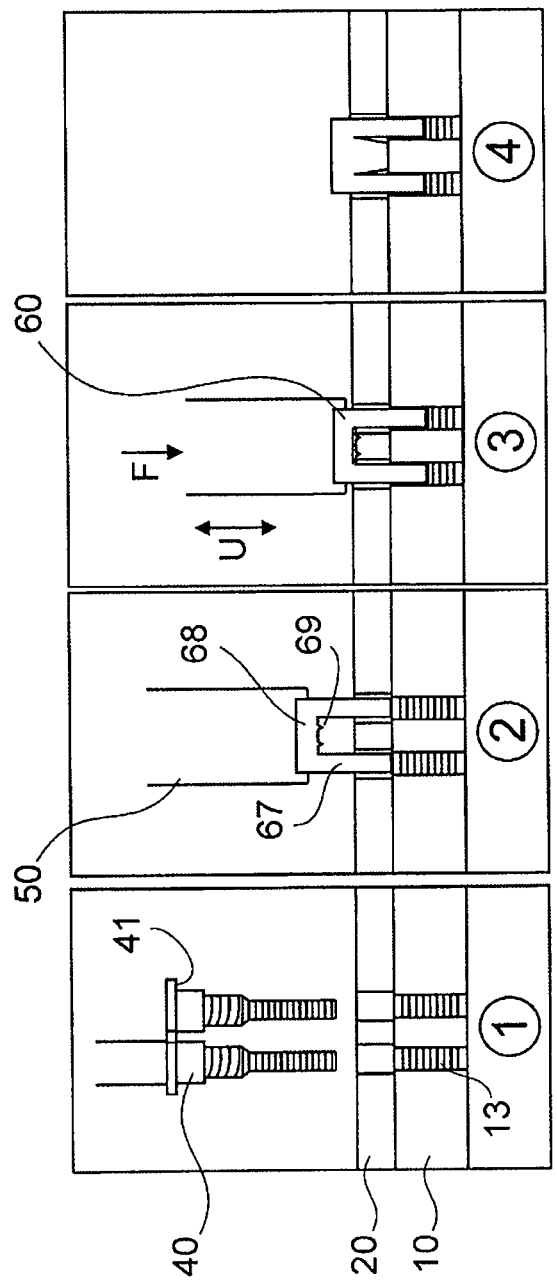
FIG. 10 shows schematically a tenth exemplary embodiment of a method in accordance with the invention.

FIG. 10 shows the tenth exemplary embodiment of the invention. In contrast to the embodiments described above, the openings 13 of the tenth embodiment are formed in pairs. FIG. 10 shows an instrument 40 with two parallel drills which are synchronized contrarily by means of a one-level gear transmission with the translation relationship of 1:1. The drills are used to make openings 13 through the implant plate 20 and the bone 10 simultaneously. The drills are inserted in the bone 10 until a stop 41 touches the implant plate 20 and prevents the drills from going any further. Openings 13 may be threaded. Next a pin 60 having cylindrical arms 67 coupled by a bridge 68 is inserted in openings 13. Arms 67 are sized for insertion in the openings 13. Next, a sonotrode 50 is brought in contact with the polymeric pin 60.

Sonotrode 50 applies a force F and an ultrasound vibration U to the polymeric pin 60 as shown in frame 3 of FIG. 10. The ultrasonic energy melts the material of the bracket 60 and the melted material flows into the threaded holes 13 formed in the bone 10. The pin also melts at the interface of the pin 60 and the implant plate 10. The melting together of the pin 60 with the implant plate 20 forms a stable system with a double anchorage in the bone 10. To promote the process of melting, spikes 69 are provided on the bridge 68. The spikes create areas of high energy density and thereby promote melting.

The method and system according to the present invention, allows fracture stabilization wherein an implant plate is mounted on a bone. The implant plate is angularly stable, i.e., the plate is attached such that it would not rotate around the attachment point. The fracture stabilization using the system and method of the invention can be carried out in combination with use of minimally invasive technology. A comparatively small operation trauma and small loss of blood as well as the reliable anchorage in an osteoporotic bone can be achieved by angularly stable fixation of implant plates on the bone. The implants keep their retention force despite unfavourable conditions encountered in case of complicated fractures until the conclusion of the healing of the fractures in the osteoporotic bone. The firm angularly stable connection between implant, joining element and the bone contributes to a considerably higher primary stability as well as to a lower rate of loosening.

It is noted that the various aspects of the system and method of the invention described in context of one embodiment can also be used in combination with the other embodiments of the system and method in which they were not explicitly mentioned. The bone can be provided with one, two, three or more holes depending on the situation of the fracture and the size of the implant plate. The use of a mark to control the positioning of the implant plate and/or the use of a jig on the implant plate or directly on the bone, for the preparing of the bone holes can be principally incorporated into each of the described exemplary embodiments. Additionally, a variation of the form (or shape) of the drilling in the implant plate and in the bone and of the form (or shape) of the implant plate itself or the polymeric pins coordinated with it, is freely eligible (and envisioned) in each of the mentioned exemplary embodiments. The bores (or holes or openings or drillings) and thus also the form (or shape) of the polymeric pin can be conical, stepped, straight, threaded or smooth or any combination thereof. The material of the implant plate as well as the pins of each embodiment might be resorbable. Further, the material might be selected from a polylactid material family, for example from PLLA or PLDLA.

In the following, exemplary embodiments of the invention are described.

A system according to a first embodiment of the invention, for angularly stable fixation of an implant to a bone, comprises a tool for preparing at least one hole in the bone, a sonotrode, a jig for the tool to prepare the at least one hole in a desired position and/or for the sonotrode, and an implant having a material which is fluidizable by means of the sonotrode, to angularly stable fixing the implant at the bone.

The tool of the system according to the first embodiment may be selected from the group consisting of a bone drill, a conical bone drill, a threaded bone drill, a conical threaded bone drill, a double bone drill, a stepped bone drill, a bone drill with a triangle cross section, a bone drill with an asymmetrical cross section, and a Kirschner wire.

The system according to the first embodiment may further comprise a joining element to join the implant with the corticalis, wherein the joining element may comprise a material which is fluidizable by means of the sonotrode. Further, the joining element may be selected from the group consisting of a pin, a conical pin, a dowel, a snap-fit dowel, a multi tooth dowel, a screw, a conical screw, a double pin, a stepped pin, a triangular pin, an asymmetrical pin and a pin having a thickened head. Further, the material of the joining element may be selected from PLLA material or PLDLA material.

A first method of using the system according to the first embodiment, for angularly stable fixation of an implant plate to a bone, comprises the steps of preparing at least one hole in the bone; using a jig to prepare the at least one hole in the bone; positioning the implant plate at a desired position at the bone; and joining the implant plate angularly stable with the bone.

The first method may further comprise the step of using the jig to lead means for joining the implant plate angularly stable with the bone, wherein the means for joining the implant plate angularly stable with the bone may be a sonotrode.

The first method may further comprise the step of setting a mark to define the desired position of the implant plate at the bone.

The first method may further comprising the step of fluidizing the implant plate material so that the implant plate material flows into the at least one hole in the bone, to join the implant plate with the bone, wherein the implant plate material may be fluidized by means of a sonotrode.

The first method may further comprise the step of inserting a joining element through the implant plate and into the at least one hole in the bone, to join the implant plate with the bone, wherein the implant plate and the joining element may be melted together, wherein the implant plate and the joining element may be melted together by means of a sonotrode.

The first method may further comprise the step of preparing at least one through hole in the implant plate simultaneously with the at least one hole in the bone.

A second method of using the system according to the first embodiment of the invention, of fracture fixation comprises the steps of placing an implant on the bone, the implant having a first vertical axis normal to a top surface of the implant; drilling a first hole and a second hole in the bone, the first hole and the second hole forming a first angle and a second angle respectively with the vertical axis; melting at least a portion of the implant; pushing the melted implant material in the first hole and the second hole; and allowing the melted implant material to solidify in the first hole and the second hole to obtain an angularly stable attachment of the implant to the bone, wherein the melting may be done by applying energy selected from a group consisting of ultrasonic energy and heat energy, wherein the pushing may be accomplished by a force exerted by an implement applying the energy.

A third method of using a system according to a first embodiment of the invention, of fracture fixation comprises the steps of placing a plate on a bone; forming a threaded opening in the bone; melting the plate by application of energy and flowing the melted material of the plate in the first opening and the second opening to form a angularly stable connection between the plate and the bone upon solidification, wherein the openings may be formed using a drill selected from a group consisting of a threaded bone drill, a conical threaded bone drill and a stepped bone drill, wherein the melting may be done by applying energy selected from a group consisting of ultrasonic energy and heat energy, and wherein the flowing may be accomplished by a force exerted by an implement applying the energy.

A system in accordance with a second embodiment of the invention, for fracture fixation comprises a plate, the plate having an opening, the opening being adapted to align with a hole in a bone, and the opening being rotationally non-symmetric; a drill, the drill being adopted to form the opening and the hole in the bone adjacent the plate; a jig, the jig being adapted to guide the drill, a pin insertable in the opening and the hole; and a sonotrode, the sonotrode being adapted to apply energy to the pin so as to melt at least a portion of the pin thereby attaching the pin in the bone and to the plate such that rotational movement of the plate is prevented.

The pin of the system according to the second embodiment may have a bore along its longitudinal axis, wherein the bore may be threaded and adapted to receive a threaded tip of the sonotrode. The pin may have a head and a body, wherein at least a portion of the body is conical and at least a second portion of the body is cylindrical. The pin may have a head and a body, wherein at least a portion of the body has projections. In the body of the pin, a slot may be formed.

A method of using the system according to the second embodiment of the invention, of fracture fixation comprises the steps of placing a plate on a bone; placing a jig on the plate to guide a drill to form the opening; marking the bone to locate the jig on the plate; forming at least one opening in the plate and the bone, the opening being rotationally non-symmetric; inserting a pin in the opening; and applying energy to the pin to melt at least a portion of the pin thereby attaching the pin in the bone and to the plate such that rotational movement of the plate is prevented.

The opening may be formed using a drill selected from a group consisting of a bone drill, a conical bone drill, a threaded bone drill, a conical threaded bone drill, a double bone drill, a stepped bone drill, a bone drill with a triangle cross section, a bone drill with an asymmetrical cross section, and a Kirschner wire.

The energy may be applied in the form of ultrasonic energy or heat energy.

The pin may be selected from a group consisting of a conical pin, a dowel, a snap-fit dowel, a toothed dowel, a screw, a conical screw, a double pin, a stepped pin, a triangular pin, an asymmetrical pin and a pin having a thickened head.

Furthermore, the shape of the pin and the openings may be complimentary, wherein the pin is sized to be a close fit in the openings.

According to a third embodiment of the invention, an angularly stable implant for fracture fixation, comprises a plate adapted to mount on a bone, the plate and the bone having a first opening and a second opening respectively, the first opening and the second opening being substantially aligned and having a rotationally non-symmetric shape; and a pin shaped to be inserted in the first opening and second opening and capable of receiving energy to melt at least a portion of the pin, wherein the melted material of the pin is capable of solidifying in the first opening and the second opening to weld the pin to the bone and the plate to form an angularly stable implant that does not rotate with respect to the bone.

In accordance with the first, second and third embodiment of the invention, the implant or plate as well as the joining element or pin may be made from a material selected from PLLA or PLDLA, respectively.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A system for angularly stable fixation of a bone plate to a bone having a non-cylindrical opening therein for fracture fixation, the system comprising:
    a sonotrode having a threaded tip;
    a plate adapted to mount on the bone, the plate having a first non-cylindrical opening, the plate having a first non-cylindrical opening extending along a first axis, the plate first non-cylindrical opening capable of being substantially aligned with the non-cylindrical opening in the bone; and
    a pin comprising a portion having a non-circular cross-section perpendicular to a pin longitudinal axis the pin capable of being inserted through the plate first opening into the bone non-cylindrical opening and capable of receiving energy to melt at least a portion of the pin, wherein the melted material of the pin is capable of solidifying to weld the pin to the bone and the plate to form an angularly stable implant that does not rotate with respect to the bone, wherein the pin has a bore along its longitudinal axis, wherein the bore is threaded and adapted to receive the threaded tip of the sonotrode.

2. The implant of claim 1, wherein the pin with the threaded bore and non-circular cross-section is selected from a group consisting of a conical pin, a dowel, a snap-fit dowel, a toothed dowel, a screw, a conical screw, a double pin, a stepped pin, a triangular pin, an asymmetrical pin or a pin having a thickened head.

3. The implant of claim 1, wherein the pin has a head and a body, and at least a first portion of the body is conical and at least a second portion of the body is cylindrical.

4. The implant of claim 1, wherein the pin has a head and a body, and at least a portion of the body has projections.

5. The implant of claim 3, wherein a slot is formed in the body of the pin.

6. The implant of claim 5, wherein a slot is formed in the body of the pin.

7. The implant of claim 5, wherein the shape of the pin and the first and second openings are complimentary and the pin is sized to be a close fit in the openings.

8. A system for angularly stable fixation of a bone plate to a bone having a bore with a non-cylindrical cross-section for fracture fixation, the system comprising:
    a sonotrode having a threaded tip;
    a plate adapted to mount on a bone having an opening with a non-cylindrical cross-section, the plate having a first opening, the first opening capable of being aligned with the non-cylindrical opening in the bone and having a non-cylindrical cross-section producing a rotationally non-symmetric shape; and a pin having a non-cylindrical cross-section shaped to be inserted in the first opening of the plate when mounted on the bone and capable of receiving energy to melt at least a portion of the pin, wherein the melted material of the pin is capable of solidifying in the first opening and in the non-cylindrical opening in the bone to weld the pin to the bone and the plate to form an angularly stable implant that does not rotate with respect to the bone, wherein the pin has a bore along its longitudinal axis and wherein the bore is threaded and adapted to receive the threaded tip of the sonotrode.

9. The angularly stable implant as set forth in claim 8, wherein the plate is made of a meltable material.

10. The angularly stable implant as set forth in claim 8, wherein the pin has a head and a body and at least a first portion of the body has the non-cylindrical cross-section and at least a second portion of the body is cylindrical.

11. The implant of claim 10, wherein a slot is formed in the body of the pin.

12. The angularly stable implant as set forth in claim 8, wherein the pin is selected from a group consisting of a conical pin, a screw, a conical screw, a double pin, a stepped pin, a triangular pin, an asymmetrical pin or a pin having a thickened head.

13. The system of claim 8, wherein the shape of the attachment element and the hole is complimentary and the pin is sized to be a close fit in the first and second openings.

14. The implant of claim 8, wherein the pin has a head and a body, and at least a portion of the body has projections.

* * * * *